US008502876B2

(12) United States Patent
Wang et al.

(10) Patent No.: US 8,502,876 B2
(45) Date of Patent: Aug. 6, 2013

(54) AUDIO, VISUAL AND DEVICE DATA CAPTURING SYSTEM WITH REAL-TIME SPEECH RECOGNITION COMMAND AND CONTROL SYSTEM

(75) Inventors: Gang Wang, Goleta, CA (US); Matteo Contolini, Santa Barbara, CA (US); Chengyi Zheng, Goleta, CA (US); Heinz-Werner Stiller, Jestetten (DE)

(73) Assignee: Storz Endoskop Producktions GmbH (DE)

( * ) Notice: Subject to any disclaimer, the term of this patent is extended or adjusted under 35 U.S.C. 154(b) by 1822 days.

(21) Appl. No.: 11/519,315

(22) Filed: Sep. 12, 2006

(65) Prior Publication Data

US 2008/0062280 A1   Mar. 13, 2008

(51) Int. Cl.
*H04N 5/228* (2006.01)
(52) U.S. Cl.
USPC ......... 348/222.1; 348/373; 348/374; 348/375
(58) Field of Classification Search
USPC ............. 348/207.1, 222.1, 373–375; 704/725
See application file for complete search history.

(56) References Cited

U.S. PATENT DOCUMENTS

| 5,649,060 A | 7/1997 | Ellozy et al. | |
|---|---|---|---|
| 5,970,457 A | 10/1999 | Brant et al. | 704/275 |
| 5,995,936 A * | 11/1999 | Brais et al. | 704/275 |
| 6,266,635 B1 | 7/2001 | Sneh | 704/235 |
| 6,278,975 B1 | 8/2001 | Brant et al. | 704/275 |
| 6,463,361 B1 | 10/2002 | Wang et al. | 700/258 |
| 6,499,016 B1 | 12/2002 | Anderson | |
| 6,587,818 B2 | 7/2003 | Kanevsky et al. | 704/251 |
| 6,591,239 B1 | 7/2003 | McCall et al. | 704/275 |
| 6,601,026 B2 | 7/2003 | Appelt et al. | 704/9 |
| 6,642,836 B1 | 11/2003 | Wang et al. | 340/3.54 |
| 2001/0025241 A1 | 9/2001 | Lange et al. | |
| 2002/0183894 A1 | 12/2002 | Wang et al. | 700/245 |
| 2003/0063321 A1 | 4/2003 | Inoue et al. | |
| 2003/0197590 A1 | 10/2003 | Wang et al. | 340/3.54 |
| 2004/0124964 A1 | 7/2004 | Wang et al. | 340/3.54 |
| 2004/0172011 A1 | 9/2004 | Wang et al. | 606/1 |
| 2006/0142739 A1 | 6/2006 | DiSilestro et al. | |

FOREIGN PATENT DOCUMENTS

| EP | 0699941 A1 | 3/1996 |
|---|---|---|
| EP | 0965979 A1 | 12/1999 |
| EP | 1172064 A2 | 1/2002 |

(Continued)

OTHER PUBLICATIONS

Extended European Search Report; EP 07 01 5333; Jun. 22, 2009; 9 pages.

(Continued)

*Primary Examiner* — Yogesh Aggarwal
(74) *Attorney, Agent, or Firm* — St. Onge Steward Johnston & Reens LLC (57) ABSTRACT

An audio, visual and device data capturing system including an audio recorder for recording audio data, at least one visual recorder for recording visual data, at least one device data recorder for receiving device data from at least one device in communication with the system, a speech recognition module for interpreting the audio data, a transcript module for generating transcript data from the interpreted audio data, a data capturing module for generating a data record including at least a portion of each of the audio data, the transcript data, the visual data and the device data, and at least one storage device for storing the data record.

32 Claims, 5 Drawing Sheets

FOREIGN PATENT DOCUMENTS

| | | |
|---|---|---|
| JP | 2002207753 A | 7/2002 |
| JP | 2002336184 A | 11/2002 |
| JP | 2003044085 A | 2/2003 |
| JP | 2004507941 T | 3/2004 |
| JP | 2005135344 A | 5/2005 |
| WO | 0111607 A1 | 2/2001 |
| WO | 0158165 A2 | 8/2001 |
| WO | 0217640 A1 | 2/2002 |

OTHER PUBLICATIONS

European Office Action; Application No. 07 015 333.3-2225; Feb. 26, 2010; 5 pages.

* cited by examiner

AUDIO, VISUAL AND DEVICE DATA CAPTURING SYSTEM WITH REAL-TIME SPEECH RECOGNITION COMMAND AND CONTROL SYSTEM

FIELD OF THE INVENTION

The invention relates to audio, visual and device data capturing, and more specifically to an audio, visual and device data capturing system including speech recognition for real-time data transcription. Even more specifically, the present invention relates to audio-visual and device data capturing for medical, technical, and scientific applications, including speech recognition for real-time data transcription integrated into a command and control system.

BACKGROUND OF THE INVENTION

Audio-visual data capturing has been implemented in some command and control systems, such as operating room control systems. For example, devices such as the Karl Storz Advanced Image and Data Archiving System (AIDA™) allow a surgeon to capture a video stream signal or still images obtained during a surgical procedure. The image or video recording may further be annotated by a user, such as a surgeon performing an operation. Generally the voice annotations are recorded and the recordings are stored with the captured still or video image. The captured audio and visual data is generally stored in a database or on portable media (e.g., Compact Disk).

In the medical field, the captured audio and visual data may include important information related to the patient and/or the treatment being given to the patient. For example, the captured audio and visual data may be used post-surgery for obtaining additional medical information about a particular patient and for making treatment decisions. The audio and visual data may also be used for training purposes and for documenting medical procedures for potential liability causes of action. However, prior art audio and visual data capturing systems have limitations.

One disadvantage of prior art audio and visual capturing systems is that only raw audio-visual data, i.e., visual imagery and voice recordings, is captured and stored. Therefore, the usability of the data is very limited. In order to find any desired data, e.g., related to particular subject, a user must play the recording and listen and/or watch for all instances of the desired information. This is both a cost ineffective and inaccurate means to obtain the desired data. It is therefore desired to provide an improved audio and visual capturing system providing highly useable data.

A further disadvantage of prior art systems is that device status information is not captured, synchronized, and stored along with any pertinent or desired audio-visual data. Examples where this would be highly desired is where during an operation or procedure, a medical professional wishes to document a particular event; such as abnormal bleeding or other such complication. Along with the audio data being captured, transcribed, and synchronized with visual data, patient vital signs, such as those monitored by associated medical device(s), may also be captured and synchronized. Moreover, medical device operational status data, such as pump and vacuum pressures, medication levels being received by the patient, anesthesia device settings, and the like, may be captured and synchronized with the audio-visual data. Similarly, technical and scientific endeavors would also benefit from a real-time capture and synchronization of audio, visual, and device data during research and development, testing, and/or system monitoring endeavors. It is therefore desired to provide a system for capturing audio, visual and device data.

Another disadvantage of prior art systems is that dynamic or simultaneous control of equipment via a speech recognition system is difficult to achieve with add-on audio transcription sub-systems. This difficulty arises when user audio utterances, which are intended by the system user as commands to control equipment, are misinterpreted as audio data intended to be captured, synchronized, transcribed, and stored on a real-time basis. Furthermore, add-on audio transcription sub-systems lack sufficient ability to learn and adapt to new topics of conversation. In a typical system or application, language or topic changes can happen very frequently. Changes may occur slowly over time or abruptly, such as when a device is added to or removed from the system. Prior art systems are unable to properly adapt to these changes and therefore have a high initial transcription error rate.

What is highly desired then is a speech recognition command and control system, which discriminates between user audio utterances intended for equipment command and control from audio data intended for capture, synchronization transcription, and storage with other data.

SUMMARY OF THE INVENTION

According, it is an object of the present invention to provide an audio and visual data capturing system for generating a real-time transcript of voice annotations in a speech recognition command and control system.

It is a further object of the present invention to provide such a system which synchronizes the transcript with other forms of data including visual imagery, audio recordings, device status data, and the like.

It is a further object of the present invention to provide a speech recognition command and control system including an audio, visual and device data capturing application.

Still further, it is an object of the present invention to provide a speech recognition command and control system that discriminates between user audio utterances intended for command and control of device(s), from audio data for capture, synchronization, transcription, and storage with other data.

Still further, it is an object to provide a speech recognition and command control system with a highly dynamic command and control feature for adapting to changes in conversation topics or language and for updating recognition grammar accordingly.

These and other objectives are achieved by providing an audio and visual data capturing system including an audio recorder for recording audio data, at least one visual recorder for recording visual data, a speech recognition module for interpreting the audio data, a transcript module for generating transcript data from the interpreted audio data, a data capturing module for generating a data record including at least a portion of each of the audio data, the transcript data, and the visual data, and at least one storage device for storing the data record. In some embodiments, the system further includes at least one device data recorder for receiving device data from at least one device in communication with the system, wherein the data record further includes at least a portion of the device data.

Further provided is an audio and visual data capturing system with speech recognition and control including an audio recorder for recording audio data, at least one visual recorder for recording visual data, a speech recognition module for interpreting the audio data and generating transcript data, a controller for generating a control command based on at least a portion of the interpreted audio data, a data capturing module for generating a data record including at least a portion of each of the audio data, the visual data and the transcript data, and at least one storage device for storing the data record. In some embodiments, the system further includes a discriminator for distinguishing between user utterances in the audio data intended as control commands and user utterances intended as transcript data.

Further provided is a method of processing audio, visual and device data including the steps of recording audio data, the audio data including one or more user utterances, recording at least one of visual data and device data, interpreting the one or more user utterances, generating transcript data, generating a data record including at least a portion of each of the audio data and the transcript data and storing the data record. The step of interpreting the one or more user utterances optionally includes discriminating between user utterances intended as control commands and user utterances intended for transcription.

DETAILED DESCRIPTION OF THE INVENTION

Figure 1:
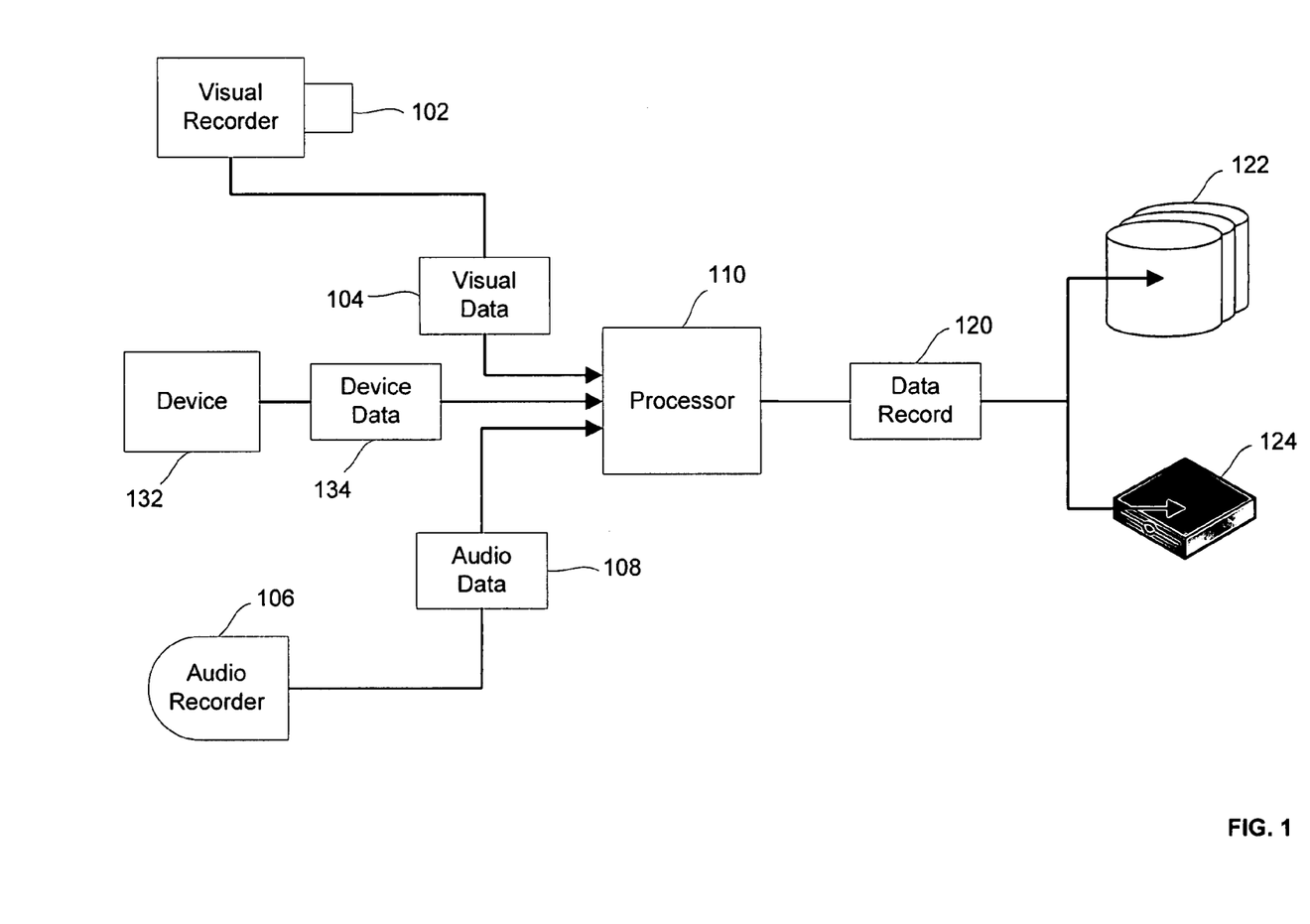
FIG. 1 is a schematic diagram of a system according to the present invention.

FIG. 1 shows an audio, visual and device data capturing system according to the present invention. The system may be useful for any number of applications including, for example, audio, visual and/or device data capturing in a medical operating room setting.

The system includes one or more visual recorders 102. The visual recorder 102 may be, for example, a video recorder for receiving and recording video imagery. The visual recorder 102 may also be a still image recorder. For example, the visual recorder 102 may be a digital camera or any other device for recording or capturing still images or photographs. The visual recorder 102 may be any shape or size. In some embodiments, the visual recorder 102 is a micro camera. The visual recorder 102 may also be handheld, mounted and/or incorporated in a device. For example, the visual recorder 102 may be in or on a medical device such as an endoscope.

The visual recorder 102 may be used to capture any visual imagery or images. For example, the visual recorder 102 may capture video imagery of a surgical procedure and/or still images of the same. The visual recorder 102 sends visual data 104 to the system or a module or processor 110 thereof. The visual recorder 102 may send visual data 104 continuously and/or in real-time, or upon user request or command. The visual recorder 102 may further send visual data 104 by any means, e.g., via a communication channel or cable (e.g., fiber optic cable) and/or a wireless connection.

The system further includes one or more audio recorders 106. The audio recorder 106 may be any instrument or device for receiving an incoming sound or sound wave and converting it into a digital waveform and/or an electric current or electric energy (e.g., audio data 108). For example, the audio recorder 106 may be a microphone. The recorder 106 may communicate information, including audio data 108, to the system via a communication channel or cable and/or wireless connection. Input received by the audio recorder 106 may be any audio input. For example, the audio input may be a spoken utterance from a user, such as a spoken word or phrase, or a collection of words or phrases. The input may further be speech annotations associated with a video or still image that a user desires for the system to store and/or document. Input to the audio recorder 106 may, in some embodiments, include spoken words or phrases indicative of one or more speech commands which a user desires to be communicated or implemented by the system. Input to the audio recorder 106 may also be any other sound and/or noise.

The system further includes one or more devices 132 operatively connected to the system. The device 132 may be, for example, medical equipment controlled by the system, such as lights sources, insufflators, vacuum pumps, video displays, or surgical tables. Additionally, the device 132 may be, for example, medical equipment connected to the system for data retrieval, such as anesthesia equipment which is not under direct speech recognition system control. For technical, industrial, or scientific applications, the device 132 may be, for example, equipment required for a specific endeavor where device control and/or data capture, synchronization, and storage is desired; such as test equipment, environmental control equipment, manufacturing equipment, or engine status and control equipment.

The device 132 sends device data 134 to the system or a module or processor 110 thereof. The device data 134 may include any data from the device 132 including, but not limited to, device status information, device settings, and/or device output(s). The device 132 may send device data 134 continuously and/or in real-time, or upon user request or command. The device 132 may further send device data 134 by any means, e.g. via a communication channel or cable (e.g. fiber optic cable) and/or a wireless connection.

The system may further include one or more processors 110. The processor 110 may be any device, collection of devices and/or components or a system that controls at least one operation or receives and/or executes one or more software programs. The processor 110 may, for example, be one of a digital signal processor, a microcontroller, a microprocessor, or a computer programmable logic device. It should be noted that the functionality associated with the processor 110 may be centralized or distributed, whether locally or remotely. The processor 110 is in communication with the audio and visual recorders 102/106, and device 132, and may receive information therefrom including visual data 104, audio data 108 and/or device data 134. The processor 110 may include and/or access any number of applications, components or modules for processing data, e.g., visual data 104, audio data 108 and/or device data 134.

The system according to the present invention also includes any number of storages, storage devices and/or storage drives. For example, the system may include one or more databases 122. The system may further include one or more portable media drives 124 and corresponding portable media. The portable media drive 124 may be any portable media or portable storage drive including, but not limited to, a 3.5" floppy disk drive, a zip disk drive, a CD writing drive, a DVD writing drive, a memory card drive (e.g., compact flash, secure digital, memory stick, etc.), a tape drive, and/or an external hard drive. Data records 120 may then be transferred to a database or remote computer using the portable media, or may be forwarded to a network storage device via a local area network (i.e., intranet) or wide area network (i.e., Internet).

As shown in FIG. 1, the storage or storages of the system may receive and store data record(s) 120 generated or updated by the system.

Figure 2:
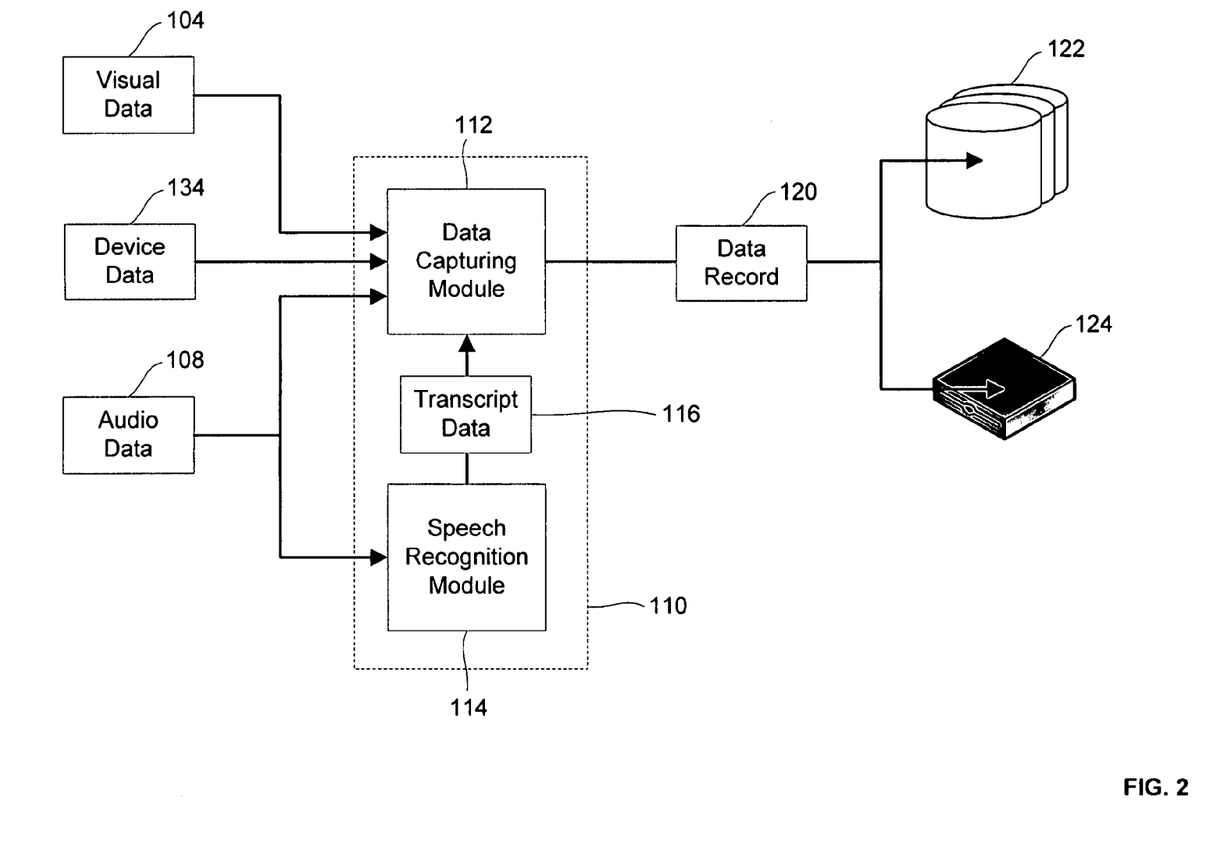
FIG. 2 is another schematic diagram of the system shown in FIG. 1.

FIG. 2 shows another schematic view of the system according to the present invention. As shown, the system may include any number of modules, components or software applications and/or processes executable by the processor 110. As one of ordinary skill in the art will understand, software of the system may be stored or located either local or remote to the processor 110, e.g., in a database and/or temporary memory (e.g., the storage 122). For example, in some embodiments, each module may be a separate hardware module including software and, e.g., a processor and/or storage.

The system includes at least one data capturing module 112 for receiving and processing audio, visual data and device data. The data capturing module 112 may be embodied in hardware, software or a combination thereof. For example, the data capturing module 112 may include data capturing software executing on the processor 110. The data capturing module 112 receives and processes data such as the audio data 108, visual data 104, and device data 134.

The system further includes a speech recognition module 114 for interpreting audio data 108 and generating transcript data 116 therefrom. For example, the speech recognition module 114 may receive the audio data 108 from the audio receiver 106 and convert the audio data 108 into a set of text words, numbers, or symbols. Interpreted data or transcript data 116 may then be sent as an input to the data capturing module 112. In some embodiments, the system further includes a transcript module (not shown) for generating the transcript data (either in combination with the speech recognition module 114 or as a separate module).

The data capturing module 112 of the present invention generates a data record 120 including the audio data 108, the transcript data 116, the visual data 104 and/or device data 134. In situations where there is no visual data 104 or device data 134, the data record 120 may include only audio data 108 (e.g., raw audio data) and the transcript data 116. The data capturing module 112 further synchronizes the data in the data record 120. Therefore, a user accessing a particular data record 120 may review all data, e.g., audio data 108, transcript data 116, visual data 104 and device data 134, pertaining to a particular time.

The data record 120 is stored in a storage 122/124, such as a medical records database or testing results database. The storage 122/124 may, in some cases, include a plurality of data records. The data records 120 are searchable, e.g. based on the content of the transcript data 116. As discussed above, the transcript data 116 is synchronized with the other forms of data such as the audio data 108, the visual data 104 and the device data 134, if any. Therefore, a user may query the data records based on a patient or patient identifier, a particular voice annotation or subject matter discussed during a treatment or surgery, a time or time period, or any other applicable search parameter. By querying the content of the transcript data 116, the user may also access synchronized and/or associated visual data 104 (e.g., video and/or still images associated with a voice annotation) and raw audio data 108 and/or device data 134.

In some embodiments, the data record 120 is stored in a location of the storage or database based on a portion of the transcript data. For example, the data record 120 may be stored in a database location corresponding to an identifier in the transcript data 116 such as patient identifier and/or a particular subject or topic. The data and/or data records may further be sorted based on content (e.g., identifiers and/or keywords) in the transcript data 116.

Figure 3:
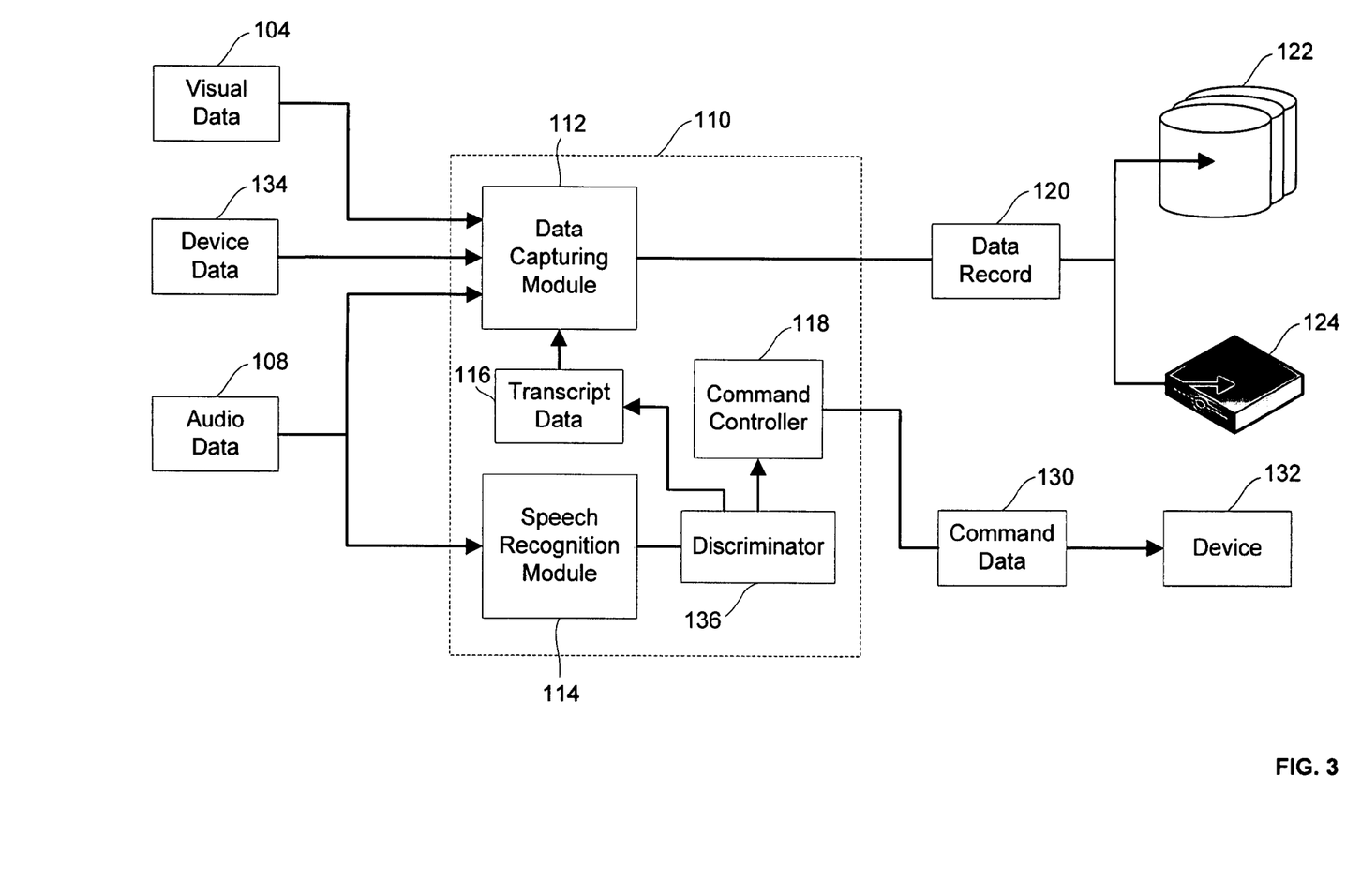
FIG. 3 is another schematic diagram of the system shown in FIG. 1.

FIG. 3 shows another schematic view of the system according to the present invention. As shown, some embodiments of the system include a command controller 118 or command module, and a discriminator 136. The command controller 118 may implement an action or generate system or device commands based on a portion of the interpreted audio data 108 via the discriminator 136. For example, a user may issue a voice command such as a command to capture a still image or to activate a visual recorder 102. The command controller 118 may then send command data 130 to a device 132 or application operable by the system and/or the particular command. The device 132 may be any device such as a medical device, instrument, tool or application. The device 132 may also be an audio recorder 106 or visual recorder 102.

The discriminator 136 determines what portions of the audio data 108 can function as speech commands, and routes such portions and/or commands to the command controller 118. The discriminator 136 may operate in different modes depending on system user preferences, such as identifying and routing speech commands to the command controller 118 while simultaneously transcribing the same speech command(s) for inclusion in the transcript data 116. Operating in such a mode, the system would allow for the control of devices via the speech recognition module 114, while transcribing in real-time all the audio data 108 desired for transcription by the system user. Conversely, the discriminator 136 may be placed in a mode where only the audio data 108 intended by the user for transcription is included in the transcription data 116 (i.e., speech commands are not transcribed and included in the transcript data 116).

The discriminator 136 and/or command controller 118 are highly dynamic and may continuously update a language model or recognition grammar accessible by the system (e.g., in the database 122) as necessary. For example, recognition grammar may be updated when a piece of controlled equipment is turned on/off, or when a voice command causes a change of position in a device control menu (e.g., menu level change). Furthermore, if a device is disconnected, the recognition grammar is promptly updated to remove commands associated with the device. As such, the present invention's integration of voice command with audio transcription provides a system in which voice commands that are intended to control equipment or devices are always properly recognized and interpreted, while voice annotations intended for transcription are absorbed by the audio transcription system.

Some embodiments of the system further include at least one user interface or graphical user interface (not shown). The user interface may be any device for displaying or otherwise providing information or feedback to a user and/or receiving input or information from the user. For example, the user interface may include any number of components such as a monitor or display, a keypad, keyboard, a touch-screen, a mouse, and/or an audio output. The user interface may display a menu, such as a tree-structured menu, including commands associated with one or more devices and/or applications of the system.

Figure 4:
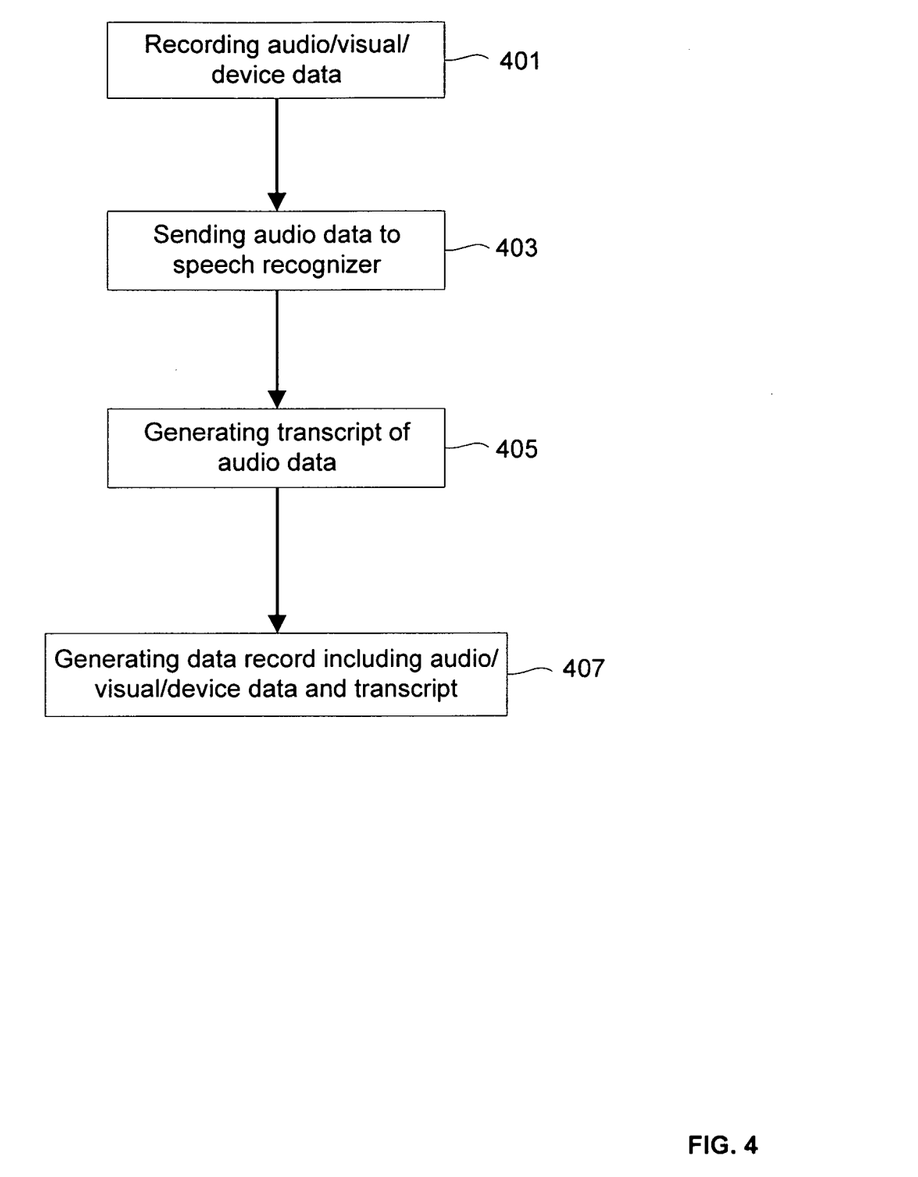
FIG. 4 is a method of processing audio, visual and device data employable by the system shown in FIGS. 1-3.

FIG. 4 shows a method of processing audio, visual and/or device data employable by the system shown in FIGS. 1-3. The method includes a step of recording audio, visual and/or device input or data (step 401). The audio, visual and/or device data may include imagery and audio input received by any number of visual recorders and/or audio recorders. The audio data is sent to a speech recognizer or speech recognition module (step 403). The audio data is interpreted and a real-time transcript or transcript data is generated therefrom (step 405). Next, a data record is generated including at least the audio data (e.g., raw audio data) and corresponding transcript data (step 407). Visual and/or device data may further be included in the data record, if any. The data in the data record is also synchronized upon generation of the data record. For example, the transcript data and/or audio data in the data record may include voice annotations synchronized to related visual and/or device data. The data record is then stored in a location accessible by the system (e.g., database or portable media device). In some cases, the data record is stored in a database location based on at least a portion of the transcript data.

Figure 5:
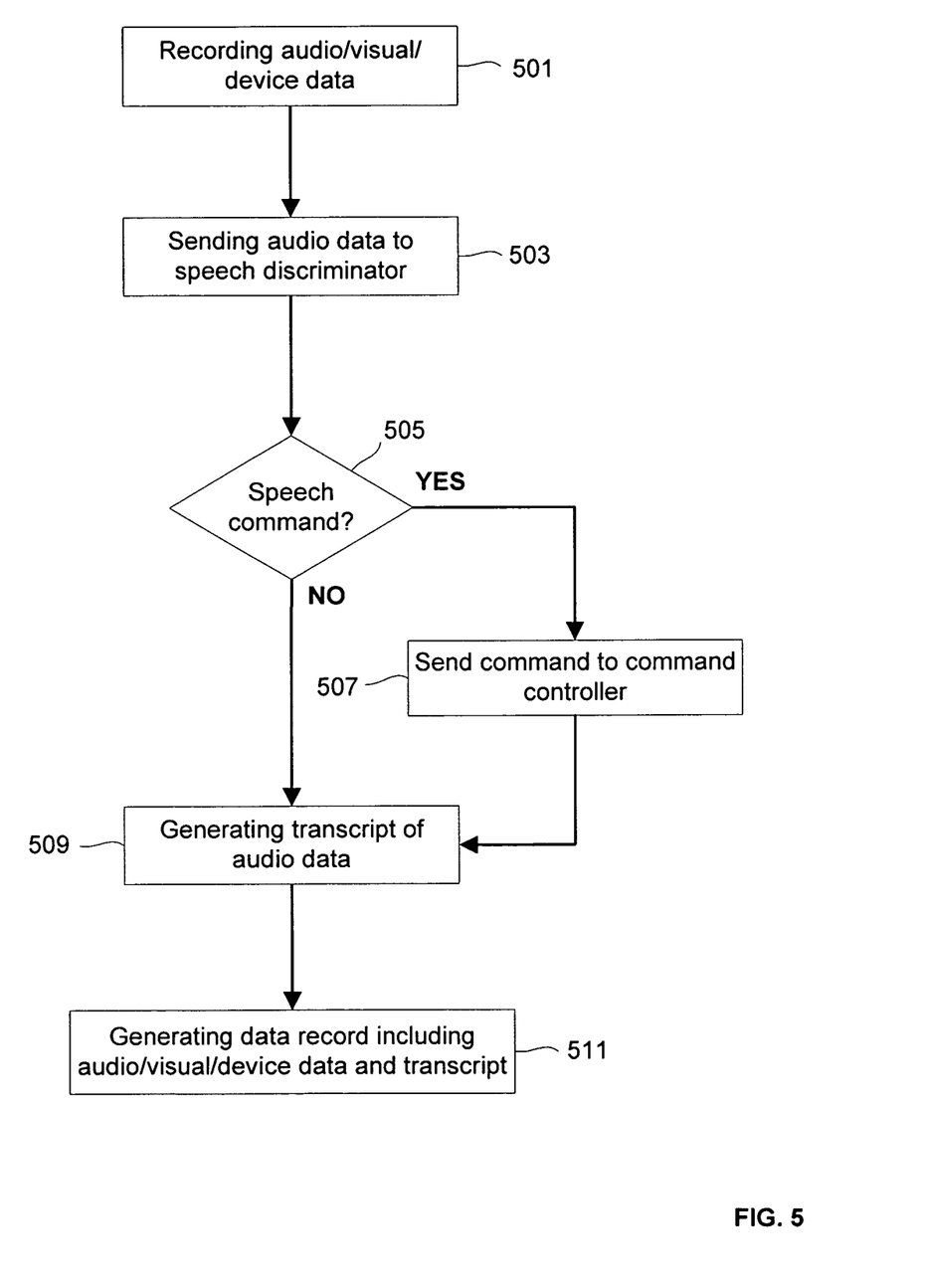
FIG. 5 is another method of processing audio, visual and device data employable by the system shown in FIGS. 1-3.

FIG. 5 shows another method of processing audio, visual and/or device data employable by the system shown in FIGS. 1-3. The method includes the steps of recording audio, visual and/or device input or data (step 501) and sending the audio data to a speech recognizer or speech recognition module for interpretation and generation of transcript data (step 503). Next, the audio data and/or transcript data may be analyzed, e.g., by the discriminator, to identify any speech commands included in the audio data and/or transcript data (step 505). If a speech command is found, the speech command or command data is sent via the command controller to an application or device operable by the particular command (step 507). The transcript is then completed (step 509). In some embodiments, the transcript data may correspond to a substantially all of the audio data. In some other embodiments and/or modes of operation, at least some of the audio data such as the speech commands are not transcribed. A data record may then be generated, e.g., including at least a portion of the raw audio data, transcript data, visual data and/or device data (step 511).

In practice, the present invention may, for example, be used to capture visual, audio and/or device data in a medical operating room. For example, the present invention may be used to capture streaming video imagery of a surgery and to record a surgeon's voice annotations to video imagery. The surgeon may make comments at a particular time pertaining to the video imagery being recorded at the time. For example, the surgeon may state: "I observed some suspicious bleeding when performing the gallbladder removal operation. The bleeding location is behind the patient's liver, which is not caused by the undergoing operation. More checking is needed." The above comments will be transcribed in real-time and synchronized and stored with the video imagery or data and/or device data. For example, the transcript and video data may be stored together in a medical record database location associated with the patient. The surgeon, or any other user, may later query the data record, e.g., using a search term such as "suspicious bleeding." Based on the search, the user can quickly locate and review the transcript data, raw audio data, and visual data or video imagery related to the suspicious bleeding noted by the surgeon.

Although the invention has been described with reference to a particular arrangement of parts, features and the like, these are not intended to exhaust all possible arrangements or features, and indeed many modifications and variations will be ascertainable to those of skill in the art.

What is claimed is:

1. An audio and visual data capturing system, comprising:
   an audio recorder for recording audio data including a plurality of user utterances;
   at least one visual recorder for recording visual data;
   a speech recognition module for interpreting the audio data;
   one or more medical devices in communication with the system;
   a discriminator for distinguishing, based on a recognition grammar, between interpreted audio data for transcription and interpreted audio data for controlling the one or more medical devices in communication with the system;
   a transcript module for generating transcript data from the interpreted audio data identified by the discriminator for transcription;
   at least one device data recorder for receiving device data, including at least one of a device status and a device setting, from at least one of the medical devices in communication with the system;
   a data capturing module for generating a data record including at least a portion of each of the audio data, the transcript data, the visual data, and the device data; and
   at least one storage device for storing the data record.

2. The system according to claim 1, wherein said data capturing module synchronizes the audio data, the transcript data, the visual data and the device data in the data record.

3. The system according to claim 1, wherein the audio data includes one or more voice annotations corresponding to one or more portions of the visual data.

4. The system according to claim 1, wherein said at least one storage device includes a plurality of data records, wherein the system comprises software for querying the plurality of data records based on the transcript data.

5. The system according to claim 1, wherein said transcript module generates the transcript data continuously while said audio recorder records the audio data.

6. The system according to claim 1, wherein said at least one storage device includes a database, wherein the data record is stored in a location of the database based on at least a portion of the transcript data.

7. The system according to claim 1, wherein said at least one storage device includes a medical records database.

8. The system according to claim 1, wherein said at least one storage device includes a portable media drive.

9. The system according to claim 1, wherein said at least one visual recorder includes a video image recorder and a still image recorder, wherein the visual data includes both still image data and video image data.

10. The system according to claim 1, wherein the one or more medical devices in communication with the system further include an endoscope, and wherein the endoscope comprises said at least one visual recorder.

11. The system according to claim 1, wherein the recognition grammar is a dynamic recognition grammar updated upon at least one of a device status change and a command menu change.

12. The system according to claim 1, wherein the data record is searchable.

13. The system according to claim 1, wherein the data record, including at least one of the transcript data and the device data in the data record, is searchable using a search parameter.

14. The system according to claim 1, wherein the one or more medical devices in communication with the system include at least one of an insufflator, a light source, a vacuum pump, a video display, and a surgical table.

15. An audio and visual data capturing system with speech recognition and control, comprising:
   an audio recorder for recording audio data including a plurality of user utterances;
   at least one visual recorder for recording visual data;
   a speech recognition module for interpreting the audio data;
   one or more medical devices in communication with the system;

a discriminator for distinguishing, based on a recognition grammar, between interpreted audio data for transcription and interpreted audio data for controlling the one or more medical devices in communication with the system;

a controller for generating a control command based on at least a portion of the interpreted audio data identified by the discriminator for controlling the one or more devices in communication with the system;

a transcript module for generating transcript data from the interpreted audio data identified by the discriminator for transcription;

at least one device data recorder for receiving device data, including at least one of a device status and a device setting, from at least one of the medical devices in communication with the system;

a data capturing module for generating a data record including at least a portion of each of the audio data, the visual data, the transcript data, and the device data; and at least one storage device for storing the data record.

16. The system according to claim 15, wherein the recognition grammar is updated upon at least one of a device status change and a command menu change.

17. The system according to claim 15, wherein the speech recognition module includes a transcript module for generating the transcript data.

18. The system according to claim 15, wherein said data capturing module synchronizes the audio data, the visual data and the transcript data.

19. The system according to claim 15, wherein said controller further sends the control command to at least one of the medical devices operable by the system.

20. The system according to claim 15, wherein the one or more medical devices in communication with the system include at least one of an insufflator, a light source, a vacuum pump, a video display, and a surgical table.

21. A method of processing audio, visual and device data, comprising the steps of:
　recording audio data, the audio data including one or more user utterances;
　receiving device data from at least one medical device, including at least one of an insufflator, a light source, a vacuum pump, a video display, and a surgical table, wherein the device data including at least one of a device status and a device setting;
　interpreting the one or more user utterances and discriminating, based on a recognition grammar, between user utterances for transcription and user utterances for controlling the at least one medical device;
　generating transcript data from the user utterances identified for transcription;
　generating a data record including at least a portion of each of the audio data, the transcript data, and the device data; and
　storing the data record.

22. The method according to claim 21, further comprising the step of:
　synchronizing the audio data and the transcript data in the data record.

23. The method according to claim 21, wherein the data record further includes the visual data, wherein the method further includes the step of synchronizing the audio data, the transcript data, and the visual data in the data record.

24. The method according to claim 23, further comprising the steps of:
　receiving a search request including at least one search parameter;
　querying the data record, including at least one of the transcript data and the device data in the data record, for the at least one search parameter; and
　providing at least a portion of the data record corresponding to the at least one search parameter.

25. The method according to claim 21, wherein the method further includes the step of synchronizing the audio data, the transcript data, and the device data in the data record.

26. The method according to claim 21, wherein said step of discriminating including querying the recognition grammar, wherein the method further comprises a step of updating the recognition grammar upon one of a device status change and a command menu change.

27. The method according to claim 21, further comprising the step of:
　sending the user utterances intended as control commands to a command controller for execution.

28. The method according to claim 27, further comprising the step of:
　sending a control command to at least one of the medical devices operable by the control command.

29. The method according to claim 21, wherein at least one of the user utterances corresponds to a portion of the visual data.

30. The method according to claim 21, wherein the data record is stored in a database location based on the transcript data.

31. The method according to claim 21, further comprising the step of:
　generating a control command based on the interpreted audio data and sending the control command to at least one of the medical devices operable by the control command.

32. The method according to claim 21, further comprising the steps of:
　receiving a search request including at least one search parameter;
　querying the data record for the at least one search parameter; and
　providing at least a portion of the data record corresponding to the at least one search parameter.

* * * * *